United States Patent [19]

Dunning et al.

[11] 4,296,756

[45] Oct. 27, 1981

[54] REMOTE PULMONARY FUNCTION TESTER

[75] Inventors: Ted E. Dunning, Denver; Paul L. Enright, Englewood, both of Colo.

[73] Assignee: Cyber Diagnostics, Inc., Denver, Colo.

[21] Appl. No.: 61,051

[22] Filed: Jul. 26, 1979

[51] Int. Cl.³ .............................................. A61B 5/08
[52] U.S. Cl. ................................... 128/716; 128/725; 128/904
[58] Field of Search ........................ 128/716, 718–720, 128/724–729, 904

[56] References Cited

U.S. PATENT DOCUMENTS

| | | | |
|---|---|---|---|
| 3,726,270 | 4/1973 | Griffis et al. | 128/719 |
| 3,819,863 | 6/1974 | Slaght | 128/904 X |
| 3,886,314 | 5/1975 | Pori | 128/904 X |
| 3,896,792 | 7/1975 | Vail et al. | 128/719 |
| 3,924,612 | 12/1975 | Dempster et al. | 128/725 |
| 3,977,304 | 8/1976 | Jones et al. | 128/728 |
| 4,034,743 | 7/1977 | Greenwood et al. | 128/725 |
| 4,129,125 | 12/1978 | Lester et al. | 128/716 X |

*Primary Examiner*—Lee S. Cohen
*Attorney, Agent, or Firm*—Klaas & Law

[57] ABSTRACT

A remote pulmonary function tester uses a microcomputer to receive patient identification data, direct the test sequence, store several FEV maneuvers, and then transmit the stored data in a digital format to a central computer. The central computer plots a flow volume curve, computes FEV, $FEF_{25-75\%}$ etc., compares these values with normals, and performs a preliminary disease categorization. The pulmonary function tester comprises a flow to pressure transducer, producing an analog signal, an analog to digital converter for digitizing the analog signal, a touch tone keyboard for simple patient identification data entry, and a microcomputer system having a read/write storage for storage of test and patient identification data, communication interface for connection to a central computer through telephone lines, and a read only memory and a central processing unit for control of the tester.

8 Claims, 13 Drawing Figures

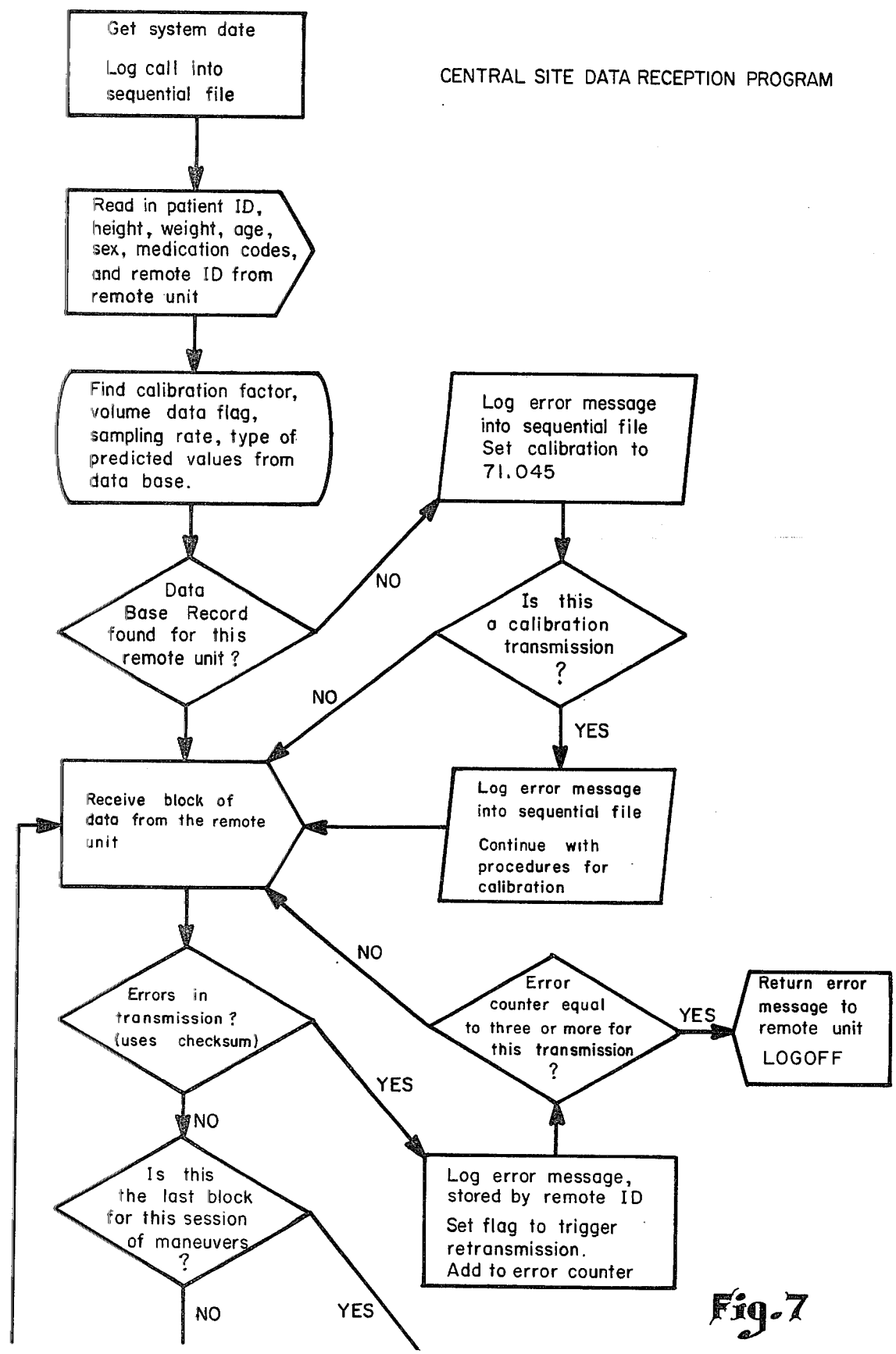

REMOTE PULMONARY FUNCTION TESTER

BACKGROUND OF THE INVENTION

The present invention relates to pulmonary function testing and, more particularly, to pulmonary function testing by a remote pulmonary function tester which communicates with a central pulmonary function analysis computer.

Pulmonary function testing (PFT) is a general term applied to a group of tests which evaluate the ability of the lungs to perform their normal functions. The most frequently used PFT is spirometry, which is the technique of measuring and recording lung volumes dynamically. Other, more complicated PFT's are usually necessary only when spirometry results are abnormal. These include body plethysmography, helium dilution, nitrogen washout, diffusing capacity, exercise testing, and blood gas analysis.

The spirometric evaluation of lung function is indicated for a number of reasons, such as: determining the presence of lung disease or abnormality of function; determining the extent of abnormality; determining the extent of disability due to abnormal lung function; determining the progression of the disease; determining the category of disease or lesion causing the abnormality; and determining a course of therapy for treatment of a previously diagnosed lung disease.

Spirometry measures two different lung functions: vital capacity and airflow rates. The vital capacity is the volume of air that can be exhaled after a maximum inhalation, measured in liters. The maneuver can be done slowly (SVC, slow vital capacity) or it can be forced (FVC, forced vital capacity). It is important because a number of diseases can result in reductions of the vital capacity. Airflow rates are measured in liters per second (L/s), during forced, or maximal expiration. Expired flows increase rapidly to a peak and then decrease with decreasing lung volume. The traditional graph, as obtained by a water spirometer, plots total volume expired vs. time. The average flow during the first second of expiration is called the $FEV_1$. It is very reproducible and has become the most frequently used flow rate measurement. $FEV_{25-75\%}$ (formerly called MMEF) is measured to give additional information about flow rates occurring later in expiration. It represents a flow rate slope between forced expiration volume at 25% and at 75% time. This flow rate measures the average flow during the middle half of the forced vital capacity maneuver and is a more sensitive indicator of mild dysfunction but is less reproducible than the $FEV_1$.

The $FEV_1$ and $FEF_{25-75\%}$ measure average flow rates. The last decade has shown increasing use of a more precise measurement of instantaneous flow rates. These are graphed by a flow volume curve, which plots flow rate (L/s) against volume (L) up to the total volume exhaled. Instantaneous flow rates at any given lung volume are readily noted on this curve, and several of these are used to compare a subject's curve, with a "normal" curve: $FEF_{max}$, $FEF_{25\%}$, (Forced Expiratory Flow at 25% of total volume) $FEF_{50\%}$, and $FEF_{75\%}$. The shape of the flow volume curve is also important in different diseases but techniques have not yet been developed to meaningfully quantitate the shape of the curves. Thus, there is needed a pulmonary function tester which provides a flow volume curve for interpretation by a chest physician.

The chest physician also compares the numerical values of the above parameters obtained for a subject's lung volumes and flow rates with normal values to determined normalcy or estimate the extent of dysfunction. Predicted normal values are obtained by studies of large populations of "normal" individuals. Normal values are best predicted by the subjects' sex, age, height, and, in the case of children, weight. The above-described parameters are conventionally calculated from the volume-time curves produced by a traditional spirometer. This technique has been recently improved by the development of pneumotac sensors, which directly measure flow rates in L/s and generate flow-volume curves. Electronic integrators are used to obtain volumes, and X-Y recorders or oscilloscopes provide graphic flow-volume curves. These systems, however, are not practical for the primary care physician due to their expense.

Another recent improvement in the field of spirometry has been the development of computerized pulmonary function testers to lessen the burden of physician interpretation of raw test data. Jones et al. in U.S. Pat. No. 3,977,394 describe a computerized unit in which a signal proportional to volume is input from a mechanical spirometer, filtered to eliminate mechanical noise, digitized at 18 samples/sec for computer processing, and used to generate, via computer, a volume time curve, FVC, $FEV_5$ (0.5 sec. after beginning of test), FEF 25-75%, and other test results. Greenwood et al., in U.S. Pat. No. 4,034,743, describe a pulmonary analyzer utilizing a piston-type spirometer and a differentiating circuit to obtain flow rate. A micro-computer is used to calculate the tidal volume and test gases breathed and to calculate FEF with a flow rate detector and volume A-D converter. These devices, however, are rather complicated and expensive and, again, beyond the means of the average physician.

It has been attempted to overcome this problem through the use of remote units connected to a central computer, as disclosed by Vail et al. U.S. Pat. No. 3,896,792 and Griffis et al. U.S. Pat. No. 3,726,270. These units, however, lack the advantages of computer preprocessing, storage, and digitization prior to data transmission. These units also utilize slow analog data transmission, which is expensive in terms of telephone costs.

Aside from the aforesaid difficulties of physician interpretation, pulmonary function testing has suffered difficulties in technician operation of the equipment and patient, or test subject, performance of the required maneuvers. Previous equipment has been difficult to maintain, calibrate, and operate. Subjects often do not give full maximum effort, or may hesitate during test maneuvers.

It is therefore an object of the present invention to provide a remote pulmonary function tester with improved patient and operator feedback.

It is further an object of the present invention to provide a remote pulmonary function tester with microcomputer-controlled data processing for transmission of data to a central computer.

It is also an object of the present invention to provide a remote pulmonary function tester which provides rapid data transmission to and from the remote unit.

SUMMARY OF THE INVENTION

The present pulmonary function tester uses a microcomputer system comprising a central processing means (CPU), a read/write memory means (RAM), communication and interface means (ACIA, modem) interconnected by a bus means. The microcomputer system is constructed and arranged to interract with other components to provide feedback, storage, and digitized data transmission functions to the pulmonary function tester.

Transducing means are provided in the form of an open-ended tube having a side tube extending transversely therein and connected to a pressure transducer for converting a test subject's flow rate into a test signal. Digitizing means then digitizes the test signal for input to the RAM of the microcomputer system. Data from several selected patient maneuvers is stored in the RAM, along with patient identification data.

Patient identification data is entered through a simple, touchtone type of keyboard in response to microcomputer-asked questions. Keys may be used for different meanings depending on the context of the data imput. Questions are asked through a display screen attached to the bus means. The display screen provides operator feedback by displaying the operator's answers. The display screen also provides patient feedback during the test maneuvers. The preferred display screen may be either a low cost single line alpha-numeric display or a graphic display comprising a cathode ray tube and graphics generator.

The present pulmonary function tester stores patient identification and test data and then rapidly transmits that data in digitized form. The stored data is transferred along the bus means to communication interface means where it is placed in a serial data stream for transmission over a single line. The communication interface means comprises signal directing means for directing a stream of patient and test data to coupling means coupled to telephone lines which are connected to the central computer. The communication interface also receives test parameters from the central computer and places them on the display screen. Coupling means may comprise either an acoustic coupler or a direct access arrangement. Tone generating means are also included in the pulmonary function tester for audio feedback from the keyboard.

BRIEF DESCRIPTION OF THE DRAWING

FIGS. 2-5 being arranged such that, when joined along their respective lines 3—3, 4—4, 4'—4', and 5—5, they form a complete schematic of the present pulmonary function tester.

FIGS. 7-13 are sequential block diagrams in the form of flow charts of the central site date reception program which form a part of the software appendix.

DESCRIPTION OF THE PREFERRED EMBODIMENT IN GENERAL

Figure 1:
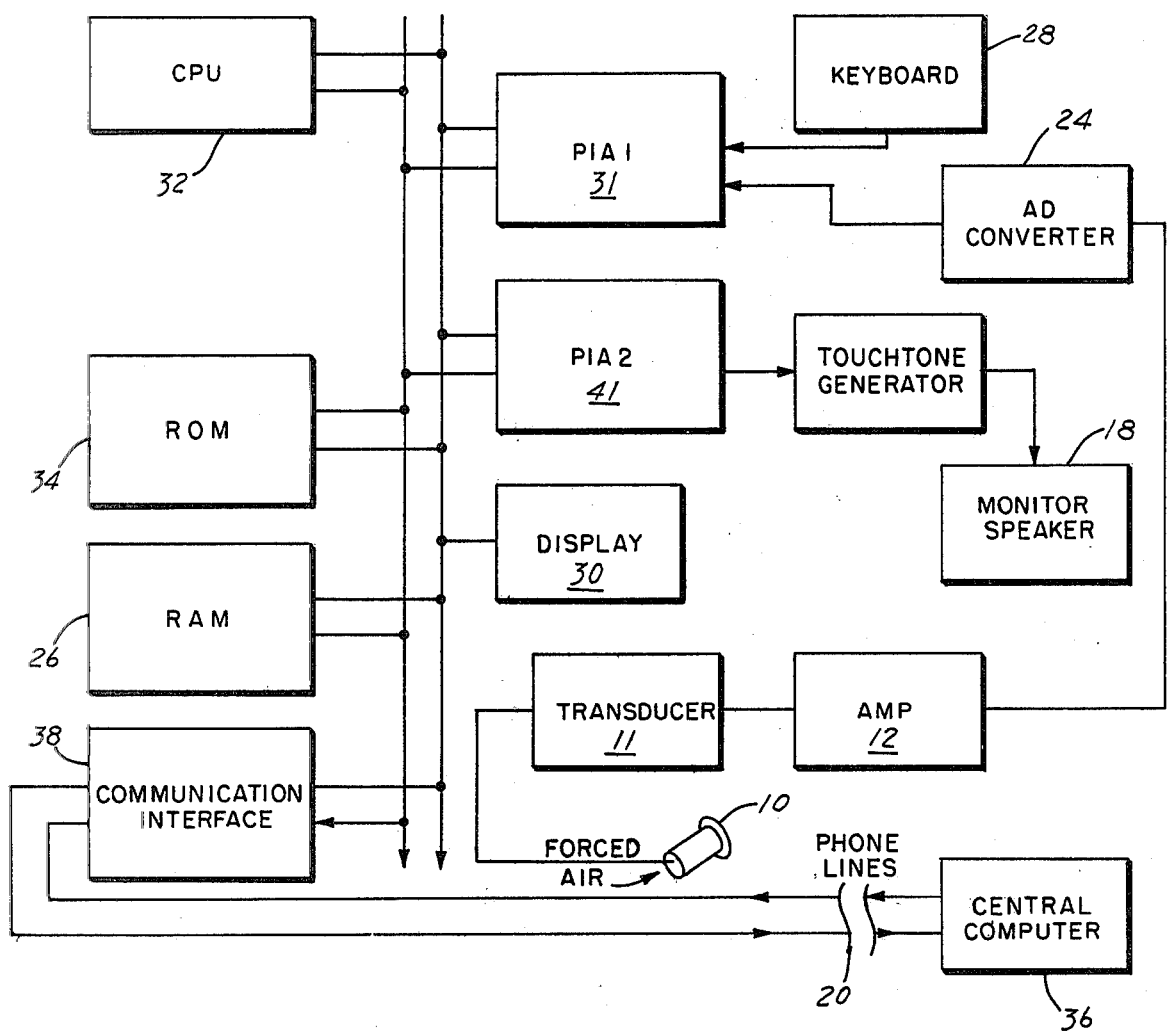
FIG. 1 is a diagrammatic block diagram of the pulmonary function tester of the present invention.

Referring now to FIG. 1, the present pulmonary function tester may be seen to comprise a flow to pressure transducer which comprises flow sensor 10 and a transducer 11 which produces a voltage proportional to the pressure exerted by the flow of air from the flow sensor. The signal from the flow transducer is passed to an amplifier 12 for buffering the signal from the rest of the tester. From the amplifier, 12, the signal is passed to a high speed analog to digital converter 24 for input to the microcomputer. The AD converter 24 converts input voltage to an equivalent digital number in response to a convert command from the microcomputer. The digitized flow data is then stored in a microcomputer read-write, or random acess, memory (RAM) 26. A real time clock measures the length of time of the flow. The digitized test data may also be directly output by passing the data through the microcomputer output system.

Aside from the above-mentioned conversion to digitized flow data, the microcomputer provides the present system with programmed operating instructions, preliminary test patient data input, and data output functions. Data input comprises information such as the test patient's age, weight, sex, etc., which is entered via a keypad 28. The keypad 28 is read and translated by a first peripheral interface adapter (PIA1) 31, displayed for operator convenience on display 30, and stored in the RAM 26. A touchtone generator 40 connected to a monitor speaker 18 provides keypad feedback to the operator. Data is output through a communication interface system 38 which comprises means for serializing parallel streams of input data for telephone transmission and for deserializing telephonic input data, (ACIA), and a modem having means for converting between digital logic levels and frequency shift-keyed telephone signals.

DATA INPUT

Figure 2:
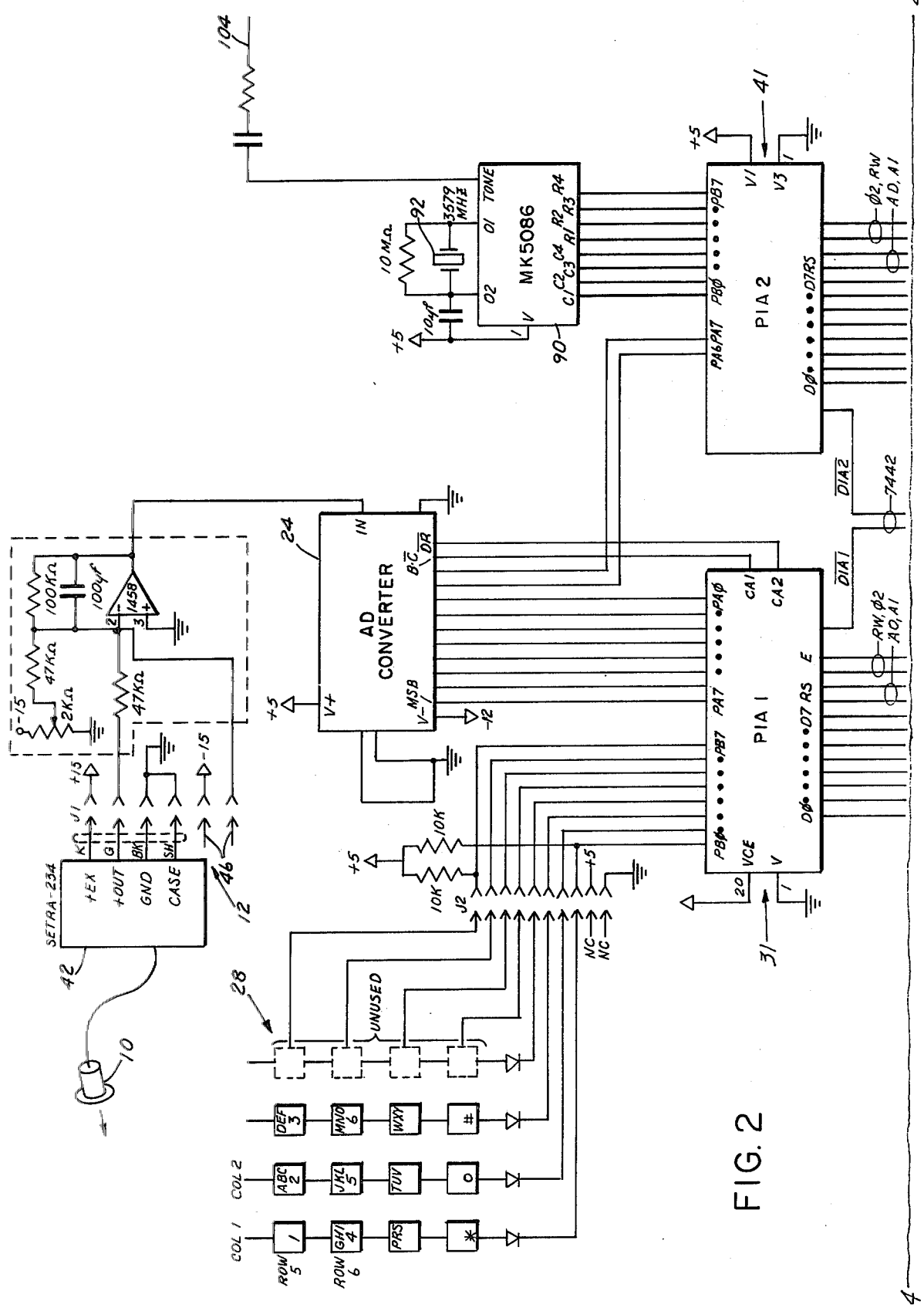
FIG. 2 is a schematic diagram representing a portion of the present pulmonary function tester broken along lines 3—3 and 4—4.

Referring now to FIG. 2, patient identificantion data is initially entered through the keypad or keyboard 28. Keyboard 28 is arranged in the form of a standard touchtone telephone keyboard of three columns numbered one through three and four rows numbered five through eight. The buttons in each row and column are connected to the PIA1 31. The keyboard 28 is conventionally internally wired so that depression of a button completes a circuit between the lines connecting the row and column wherein the button is located.

The PIA1 31 is a Motorola M6820 chip having two 8-bit I/O ports labelled PA$\phi$-7 and PB$\phi$-7 for interface to peripherals, PB$\phi$-6 being used for the keyboard for constant scanning and reading by the microprocessor according to the software appendix. Port PB7 is unused, but could be used for an extra row or column of keys. Ports PA$\phi$-7 are connected to the AD converter 24 described below. PIA1 data is input to the microprocessor external bus 64 by an 8-bit bidirectional data bus via pins D$\phi$-D7 and bus lines AO and AI through pins R and S for register selection. The PIA1 is further connected to $\Phi_2$ and R/W external data bus lines through pins E and R/W for clocking and data direction selection. The PIA1 further comprises programmable control registers and programmable data direction registers for each set of I/O ports. During system initialization, ports PB$\phi$-7 are programmed for scanning input and output and the control registers are programmed for no interrupt. Ports PA$\phi$-7 are programmed for input from the AD converter as described below.

Patient identification data may thus be entered on a twelve key keyboard scanned by PIA1. The data is placed in computer-acceptable form by the PIA1 for RAM storage or instantaneous output through the data output system.

Turning now to the test data input, the flow to pressure transducer 10 is preferably a Vanguard MP-600 transducer manufactured by Life Support Instruments. The preferred transducer, such as the MP-600, comprises an open-ended tube with one end for receiving expired air and another end with an open fiber mesh. A small venturi tube extends radially into the tube and receives pressure from air flowing through the tube. The pressure in the small venturi tube is connected by a hose to a pressure transducer 42 wherein a thin metal diaphragm is pushed towards an electrode to decrease or increase capacitance in a sensitive electric ciruclt in response to the pressure of the blow. The preferred pressure transducer is a Setra 234 with a $\pm 3$ centimeter water range. The pressure transducer 42 outputs a low voltage, about 2.5–7.5 V to the amplifier 12, which has a gain adjustment for selection of the proper output, about 5 volts. The amplifier 12 is built around a 1458 op amp as made by RCA, Motorola, and others. The op amp is also provided with extra inputs 46 for other types of transducers of either the preferred flow sensing type such as the Fleisch pneumotac or Silverman screen type pneumotach, or alternatively, volume sensing devices with electric outputs.

The amplified analog test signal from the op amp 12 is digitized with the use of a 10 bit precision AD converter 24 consisting of an AD 571 from Analog Devices, Inc.

The analog voltage level from the op amp 12 is converted to a digital number proportional to the voltage input to it. From the AD converter 24, the signal is fed through an internal digital filter to provide a smoothed output sample at 30 (thirty) times per second. The numbers are stored in the microcomputer RAM 26 and represent an accurate approximation of the analog signal, limited only by the sampling rate (4800 Hz). Time is measured by a real time clock program incorporated in NMI SRV.

In order to provide a rapid A-D sampling rate, and for other purposes hereinafter described, a baud rate of 4.8 KHz is provided by a pair of presetable up-down counters 60, 62 (FIG. 3) which input the 1 MHz clock voltage from the $\phi_2$ line of the external bus 64 and outputs a steady 4.8 KHz frequency to the BAUD line and the communications interface 38, as described below. Each counter is a 74193 chip available from a number of manufacturers such as Motorola snd Texas Instruments or other suitable device and performs the function of outputting after a discrete number of clock pulses, thus acting as a frequency divider. The first counter 60 is connected with its DN (down count) input to the $\Phi_2$ clock line and its B (borrow) and L (load) lines to the DN input of the second counter 62. The second counter outputs from its Q4 terminal to the BAUD line. The first counter is set to divide by 13 and the second by 16.

The first divider counts down from 1 MHz and outputs to the second counter, which counts down from 76 KHz and outputs to the BAUD line at 4.8 KHz ($1M \div 13 \div 16$).

DATA PROCESSING

Data processing analysis in the present unit comprises: acquiring and storing patient identification data and test data for thirty or more seconds of flow data, generally about three test blows; and control of data output.

Figure 4:
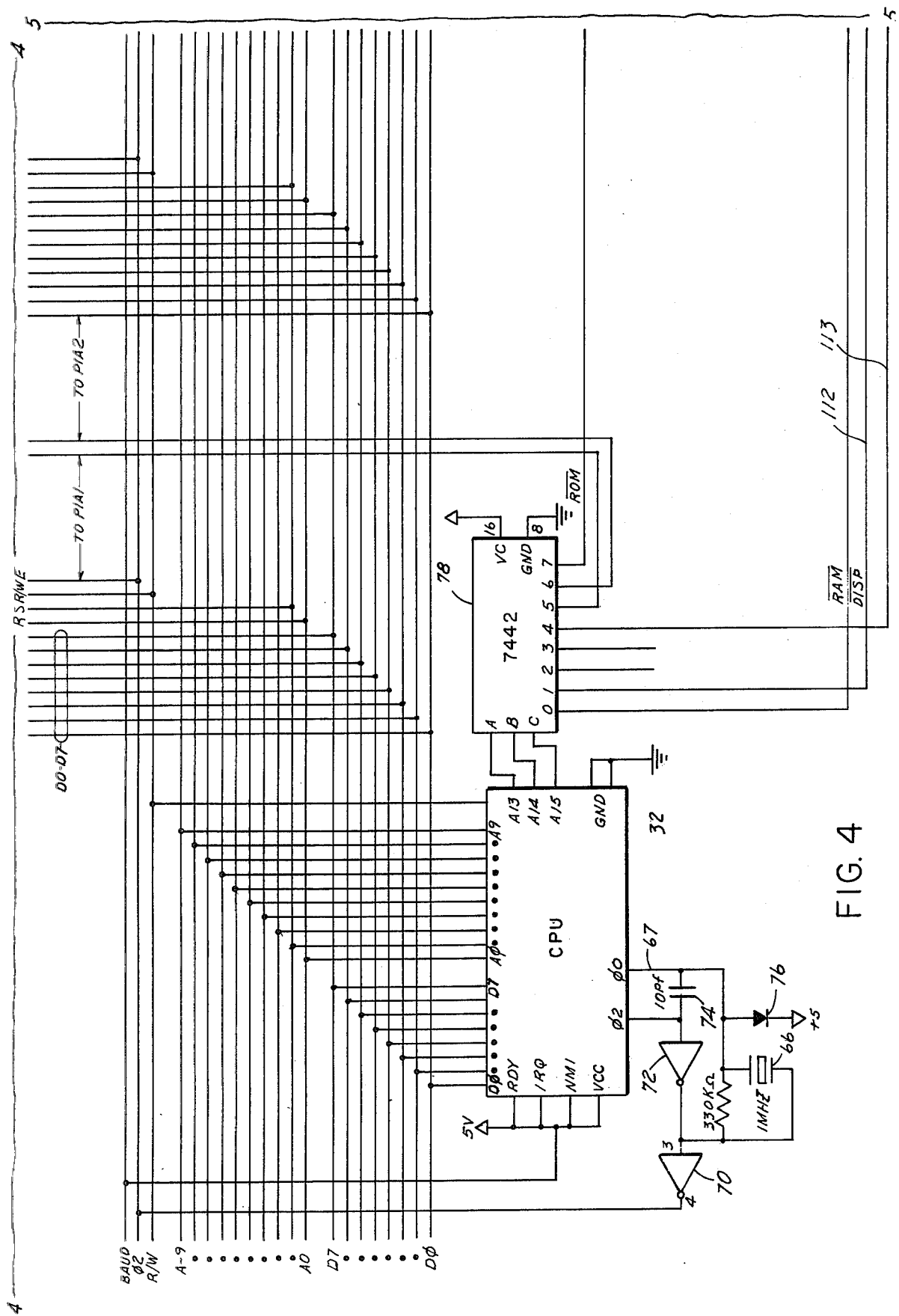
FIG. 4 is a schematic diagram of the pulmonary function tester of the present invention broken along lines 4—4 and 5—5.
Figure 5:
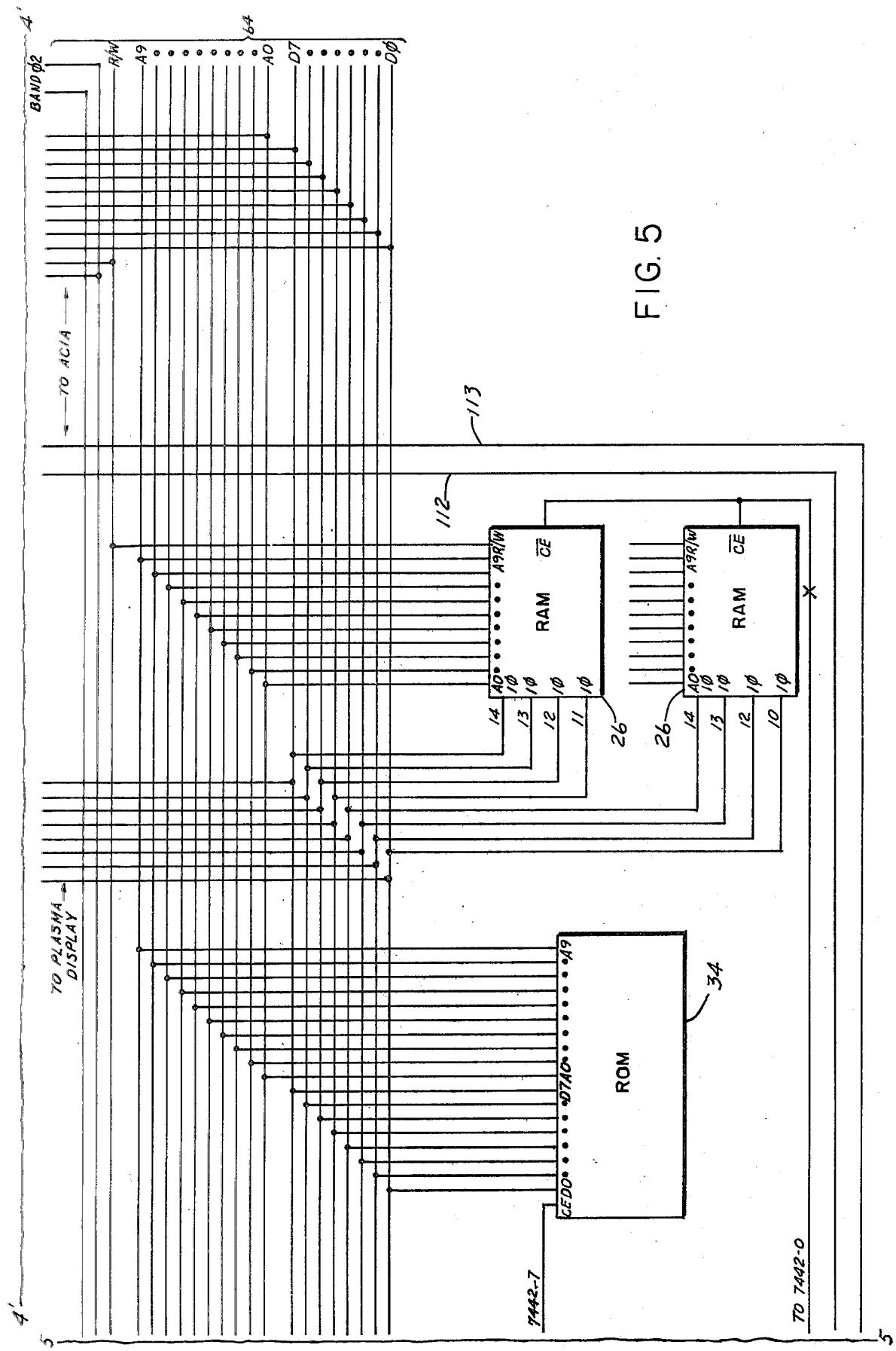
FIG. 5 is a schematic diagram of the pulmonary function tester of the present invention broken along lines 4'—4' and 5—5.
Figure 8:
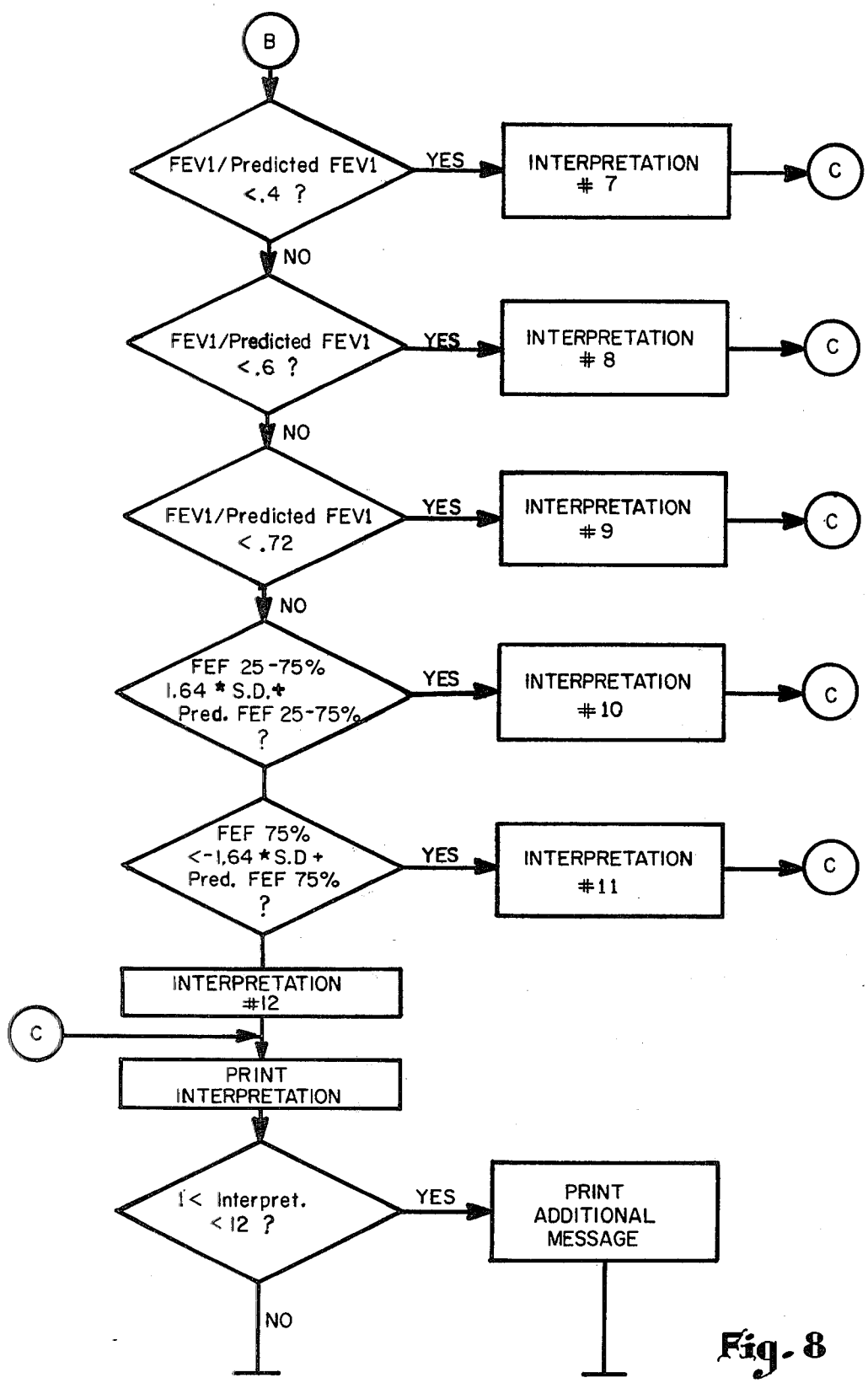
Figure 9:
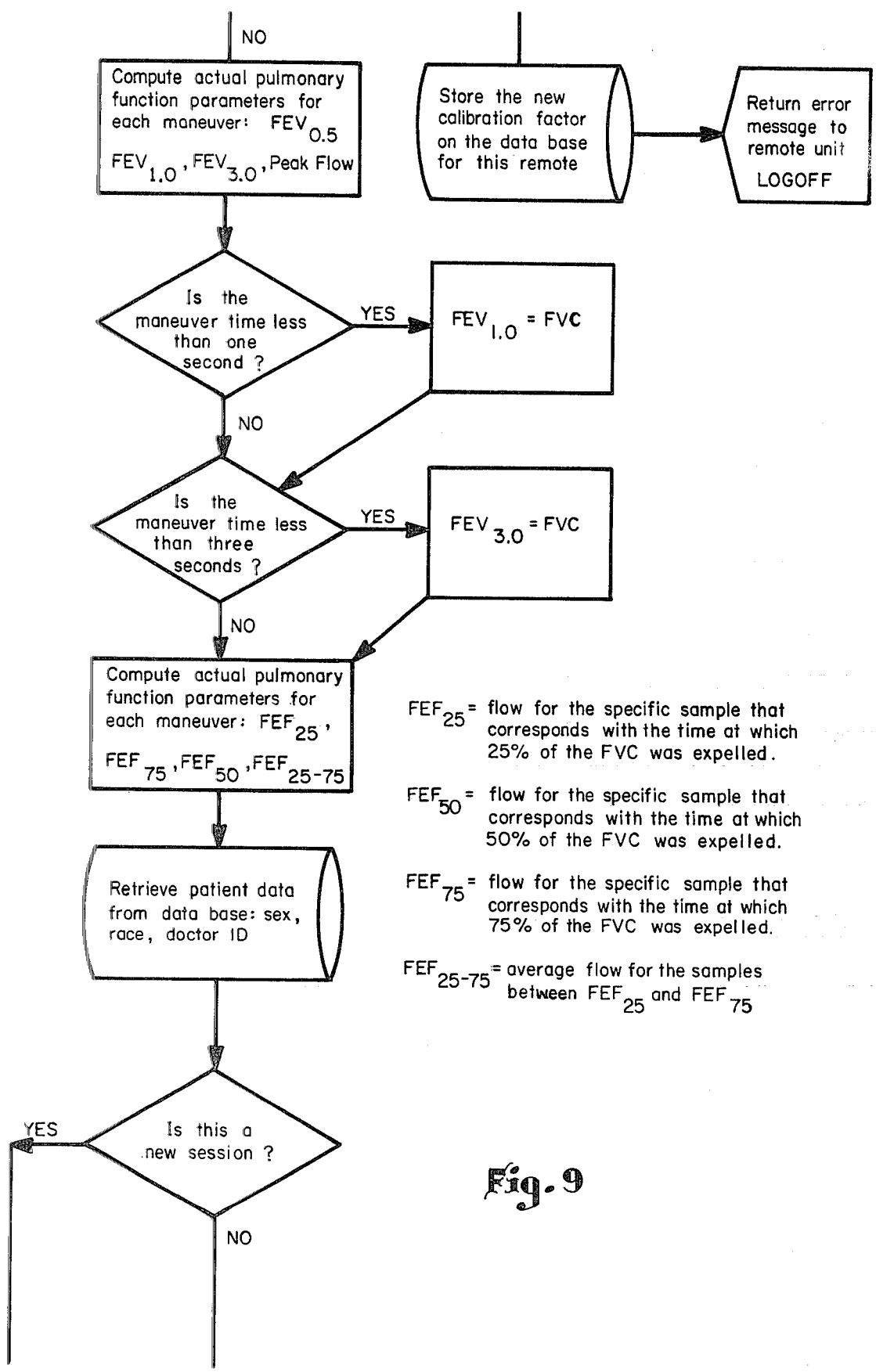
Figure 10:
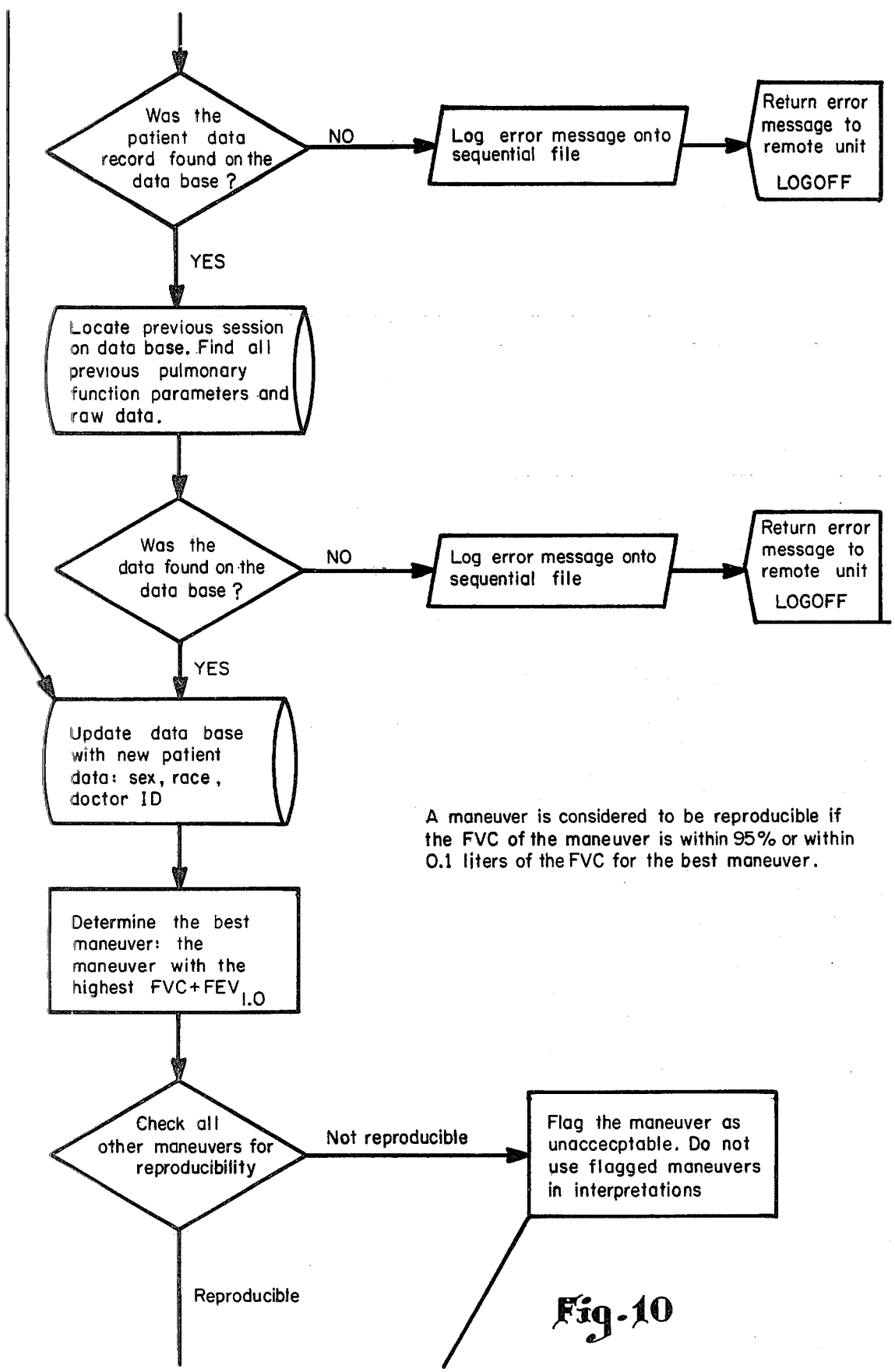
Figure 11:
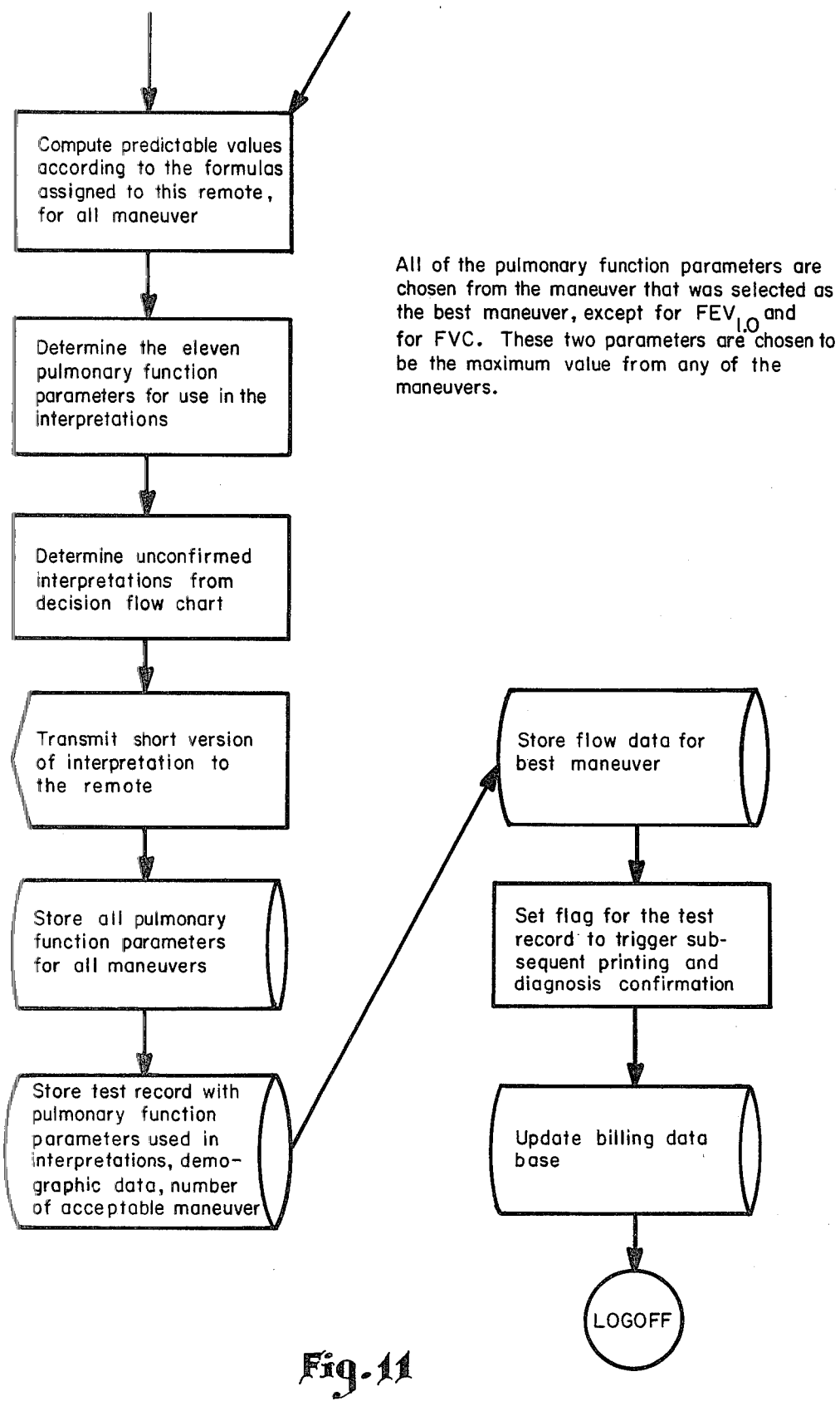
Figure 12:
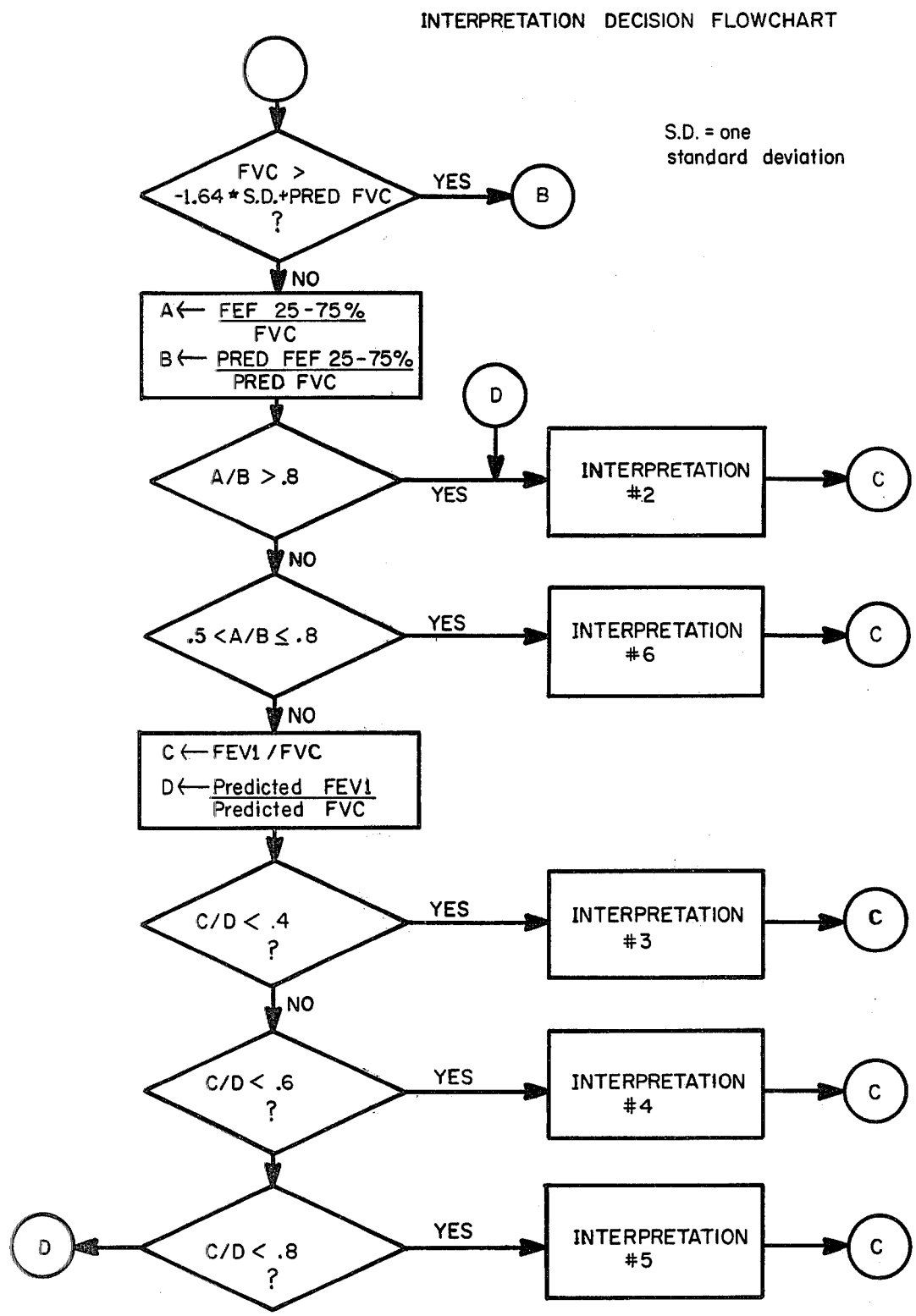
Figure 13:
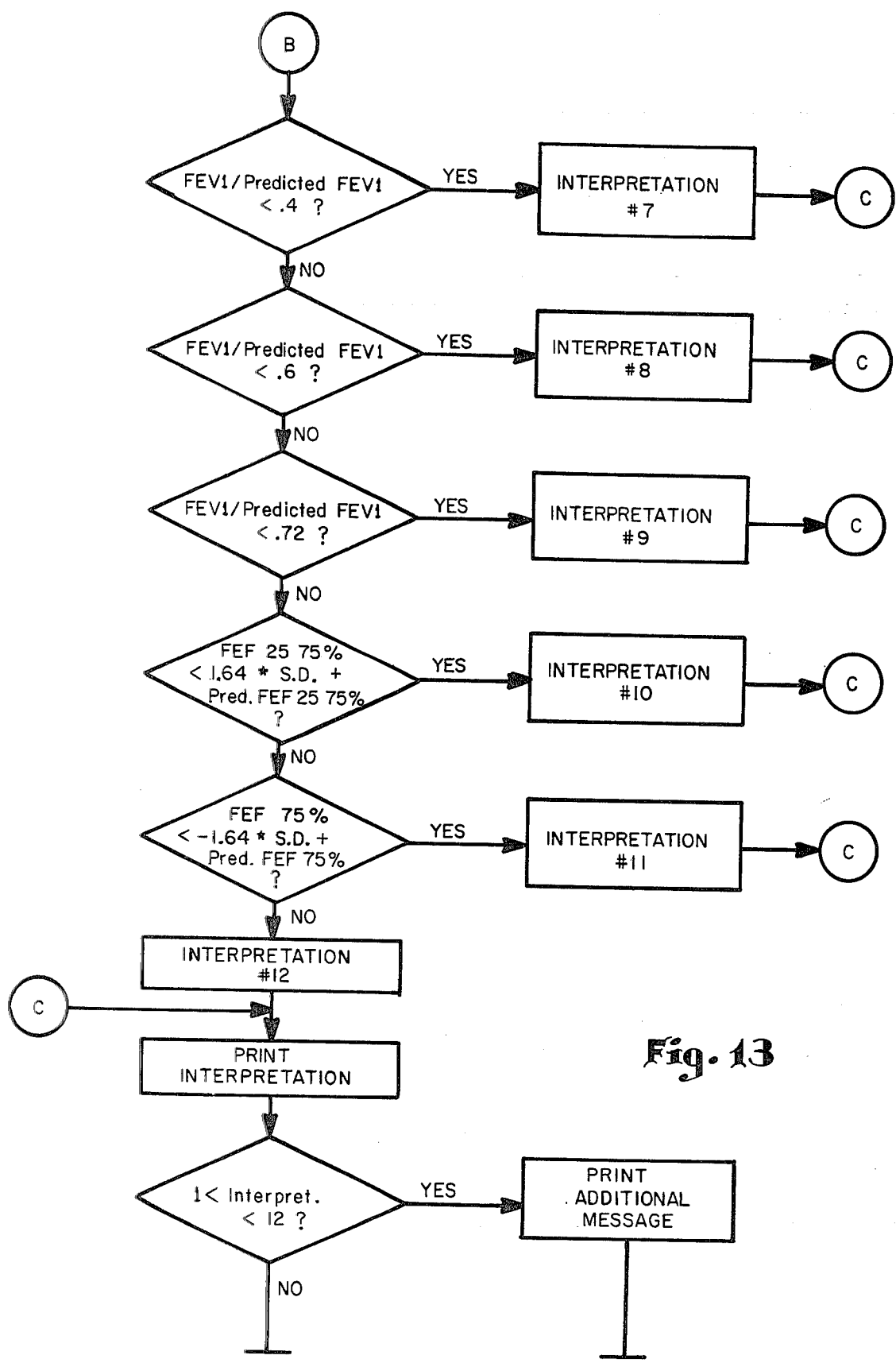

Data processing is carried out by a microcomputer system comprising the above-mentioned PIA's 31, 41, the communication interface 38, the CPU 32, the ROM 34 and a pair of RAM's 26 each connected by a data and address bus 64 (FIG. 4). The CPU 32 is an R6502 available from Rockwell and similar to and compatible with the Motorola M6800 series microcomputer components. It utilizes an input clock signal provided by a clock circuit comprising a 1 MHz quartz crystal 66 connected on one side through line 67 to the CPU $\Phi_0$ pin and on the other input of a first amplifier 70 which outputs to the $\Phi_2$ line. A second amplifier 72 is connected between the $\Phi_2$ CPU pin and the input of the first amplifier. Line 67 and the $\Phi_2$ pin are connected by a 10 pf capacitor 74. A 330K ohm resistor connects line 67 to the input side of the first amplifier 70 so that the crystal 66 is in series with amplifier 70. A diode limiter 76 on line 67 completes the clock circuit.

The CPU 32 is connected through connections D$\phi$–D7 to an 8 bit data bus, lines D$\phi$–D7 of the external bus 64. While the CPU can utilize a 16 bit wide address bus, only a 10 bit address bus in utilized in the present device. Connections A$\phi$–A9 are connected to a 10 bit wide address bus of the external bus 64. The CPU further comprises a NMI (non-maskable interrupt) input connected to the BAUD line for causing a machine state change for execution of NMI SRV and a conventional R/W (read write) output to an R/W line on the external bus 64. The Vcc (power), IRQ (interrupt request), and RDY (ready) pins of the CPU are connected to a 5 V power supply. Address connections A13–15 are connected to a chip selector device.

The chip selector device 78 comprises a 7442 decoder chip manufactured by Motorola, Texas Instruments, and others. The address output of CPU pins A13–15 is input to address input pins A, B, C, of the chip selector 78, which decodes 3 bit address codes to select various external logic components. Although the chip selector has 8 outputs, only 6 are used, with 2 spare reserved for expansion. Output O goes to the CE (chip enable) inputs of the two chip RAM 26. Output 1 goes to the WR (write) input of the plasma display 30. Output 4 goes through line 113 to the CS (chip select) input of an ACIA of the communications interface 38. Outputs 5 and 6 are connected to the CS inputs of PIA's 1 and 2, respectively. Output 7 is connected to the CE pin of the ROM 34. Each chip connected to the chip select device is selected by a 3 bit high order address code from pins A13–A15 of the CPU and is activated when the input line goes low.

The ROM 34 is a conventional 2708 chip manufactured by Motorola, Texas Instruments, and others and having 8 data output pins D$\phi$–D7 and 10 address pins A$\phi$–A9 connected to lines D$\phi$–7 and A$\phi$–9 of the external bus 64. Conventional power and ground connections (not shown) are also used. The ROM 34 has an 8K bit memory capacity organized as $1K \times 8b$ and is manufactured to store the various operating programs. If larger memory capacities are desired, a TMS 2716 PROM may be plugged into the same socket to provide 2K bytes of memory. Alternatively, a number of ROM chips may be used to increase program storage.

The RAM 26 of the present device comprises two 2114 chips manufactured by Rockwell and others and designated RAM 1 and RAM 2. The RAM's are arranged within the microcomputer system in a conventional manner. RAM 2 contains 4 I/O ports connected to lines D$\phi$-D3 and RAM 1 contains 4 I/O ports connected to lines D4-D7 of the external bus 64. Each RAM has 10 address inputs connected to the address lines of the bus and an R/W pin connected to the R/W line of the bus 64 which is in turn connected to the R/W pins of the CPU 32 and PIA's 1 and 2, 31, 41. Each RAM chip is also provided with conventional power and ground connections (not shown). Alternatively, several pairs of RAM chips may be added to increase test data storage to allow 30 seconds or more of sampling time.

The line from output O of the chip select device 78 to the CE inputs of the RAM's may be cut and an emulator microcomputer attached to the RAM inputs for trouble shooting the unit.

The data processing portion of the present pulmonary function tester thus comprises an arrangement of conventional microcomputer components in which an electronic logic unit, the CPU, coordinates the functions of the PIA's 1 and 2 memory units ROM and RAM, the display unit and the communications unit through a chip select device. The PIA's in turn control the attached keyboard, digitizing means, touchtone generator, test data input and data output.

PROCESSED DATA OUTPUT AND RECEPTION

Data output in the present device comprises patient feedback, operator feedback, and data transmission to a remote computer through a network designed also for the reception of data from the remote computer. These functions are controlled by the PIA2 41 and an asychronous communications interface adapter (ACIA) 80 comprised in the communication interface system 38.

The PIA2 41 is a Motorola 6820 chip as previously described in connection with PIA1 31. Like PIA 1, pins D$\phi$-D7 are connected to bus lines D$\phi$-D7, pins RSO and RSI are connected to lines A$\phi$ and A1 of the external bus 64, and pins R/W and E are connected to bus lines $\phi_2$. Ports PA6 and PA7 input to two low order bits from the AD converter 24. Ports PB$\phi$-7 output to pins C1-C4 and R1-R4 of a touch tone generator 90 and correspond to columns 1-4 (column 4 is unused) and rows 5-8 of the keyboard 28. The touchtone generator 90, for operator feedback, is an MK 5086 utilizing a quartz crystal 92 connected thereto in a conventional manner. The touchtone generator outputs from MKS 5086 output pin 16 through line 104 to an amplifier leading to the monitor speaker. Alternatively, a driver transistor and speaker can be directly connected to an output line to directly produce audio output. The touchtone generator generates telephone signal tones under the control of PIA2.

Operator feedback is also provided by a display module 30 comprising a DEC 220 20 character alphanumeric plasma display. This display has its own microprocessor and driving circuitry and has several modes of operation for display. The plasma display is connected 20 through data input pins D$\phi$-D7 to the data lines D$\phi$-D7 of the external bus for receiving data on those lines under the control of the PIA2. The plasma display is also provided with a connection to its WR (write) pin through a line 112 to the chip selector 78 for access to the display. The unused CS pin of the plasma display is grounded. The plasma display 30 provides operator feedback by displaying the patient data entered by the operator in response to questions asked by the microcomputer and also shown on the display. The plasma display also provides patient feedback during a test maneuver by displaying moving symbols during the maneuver. The display also displays data received from the remote computer.

Devices for display of a flow volume curve or the like from the remote computer may also be used. Hard copy printers such as an X-Y plotter or a strip chart printer, or a CRT and associated circuitry may be used as the display. Appropriate CRT equipment is a Sony Trinitron modified for direct video input in a conventional manner.

Figure 3:
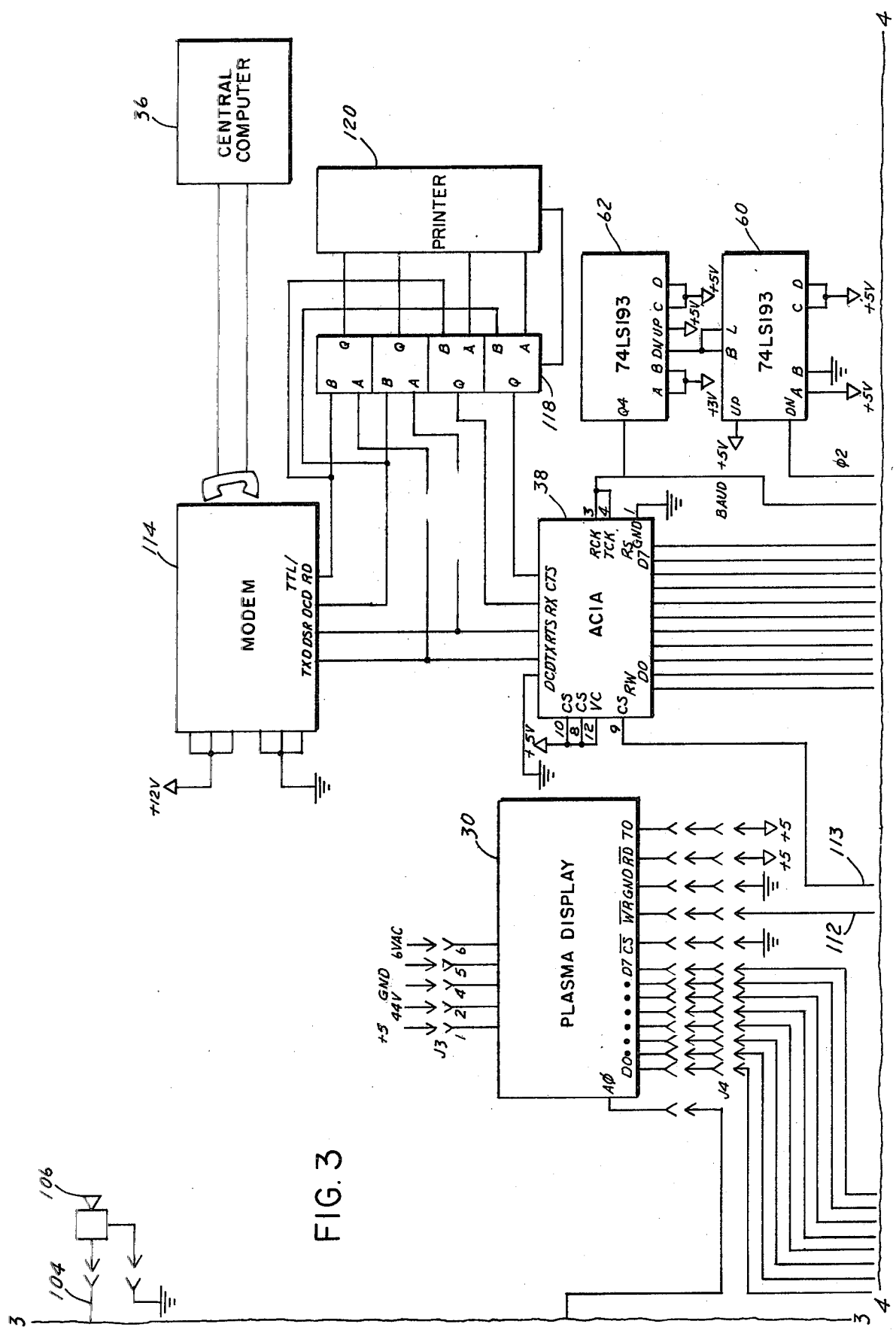
FIG. 3 is a schematic diagram representing a portion of the present pulmonary function tester broken along lines 3—3 and 4'—4'.

Turning now to data transmission and reception, data is transferred to and from the telephone lines 20 by the ACIA 80 which accepts data characters from the CPU 32 in parallel format and converts them into a serial data stream for transmission over the telephone lines and which also converts serial data into parallel format for the CPU. The ACIA is a Motorola MC 6850 having a write-only 8 bit control register programmed for a 4.8 MHz baud rate, 7 bit character lengths, no parity, 1 stop bit and no interrupts. The ACIA 80, as shown in FIG. 3, is connected through pins D$\phi$-D7 to lines D$\phi$-D7, pin R/W to line R/W, and pin $\Phi_2$ to line $\Phi_2$ of the external bus 64. The $\Phi_2$ connection provides the ACIA with a clock signal for interpreting parallel data from the RAM's, the CPU, or the PIA's. The BAUD line is connected to ACIA pins RCK (receive clock) and TCK (transmit clock) for providing the 4.8 KHz asynchronous character transmission rate. Conventional power and ground connections are also provided. The ACIA interfaces with a modem 114 through four lines connected to ACIA connection TX (Transmit Data), RTS (request to send), RX (receive data), and CTS (clear to send) to modem inputs TxD, (transmit data), and DSR (data ready), and outputs RD and DCD, respectively.

The ACIA 80 interfaces with the modem 114 through a multiplexer 118 for connecting a conventional hard copy printer 120 to the system. The multiplexer 118 is a standard 74157 chip having four segments in which each segment is switchable between one of two outputs. Through the multiplexer, data may be entered or received between the printer and either the central computer or the remote unit.

The modem 114 is an Anderson Jacobson Model AJ243. The AJ243 has built into it appropriate circuitry to provide frequency shift keying type modulation and demodulation of digital signals. This device is equivalent to an acoustic coupler connected to a set of amplifiers and filters followed by digital processing circuitry for digital data stream to audio signal conversion. Similar modems are available commercially from Recal-Vadic, Datech, and Bell. Both the modem 114 and the ACIA 80 are capable of full duplex operation, that is, they can simultaneously process incoming and outgoing data. Thus, there may be two simultaneous directions of data flow on ACIA lines D$\phi$-D7, as well as on the phone lines and from the central computer 36.

Figure 6:
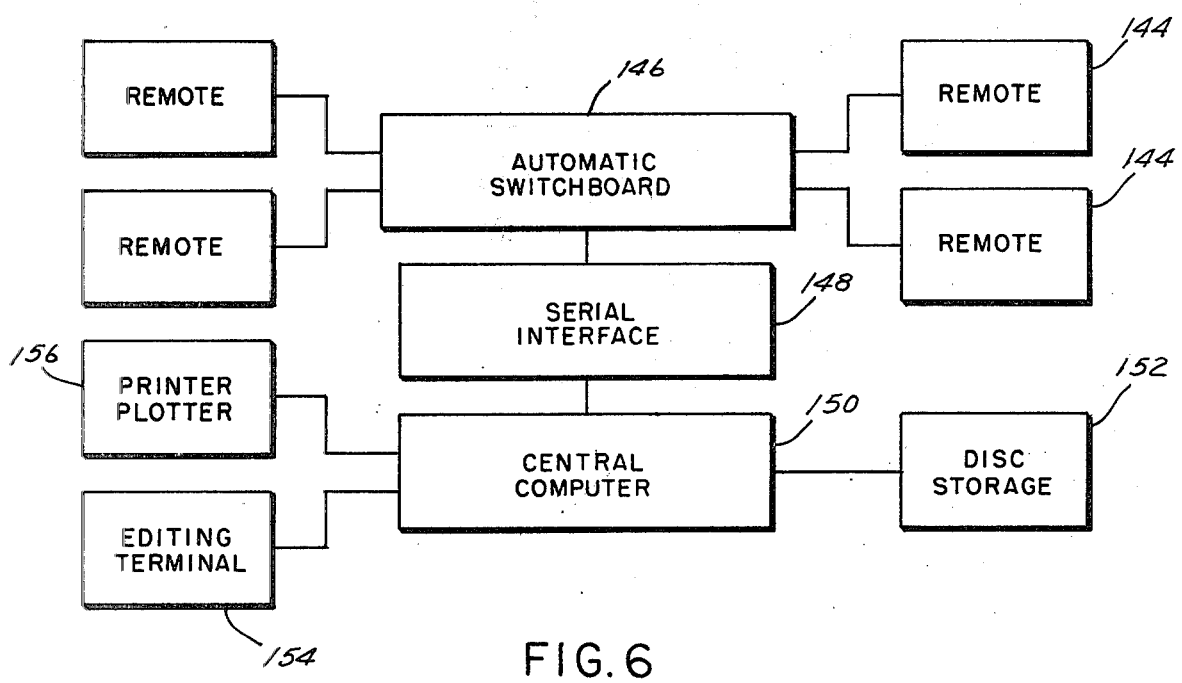
FIG. 6 is a block diagram of a central computer for use with the present pulmonary function tester.

As shown in FIG. 6, a number of remote pulmonary function testers 144 are connected through existing telephone circuits to an automatic switchboard 146. The automatic switchboard 146, as is known, automatically answers the phone in response to the remote dialing of the appropriate telephone number. The automatic switchboard can answer a number of telephone lines. The data on these lines is then serialized in a standard serial interface 148, such as an answer modem available from Vadic and others, and a standard interface such as a KD-11A from DEC, and input to the central computer 150, a minicomputer such as a PDP11 using long term disk storage 152. Data arriving at the central computer is processed according to the attached software appendix and transmitted to an editing terminal 154 such as that made by Tektronix, Lear Siegler and others. Transmission to the editing terminal may also be carried out over telephone lines. At the editing terminal, the central computer generated data interpretations are reviewed by a physician and, if necessary, revised. The revised data is then retransmitted to the central computer and fixed on a printer-plotter 156 and sent to the remote user.

The central computer interprets the data in two steps: a preliminary interpretation, which is sent immediately back to the remote unit, and a full interpretation which is sent to the editing terminal. The preliminary interpretation is carried out according to the attached appendix and includes calculation of FVC, FEV 0.5, $FEV_1$, FEV3, $FEV_1$/FVC, $FEF_{25}$, $FEF_{50}$, $FEF_{75}$, $FEF_{25-75}$, FEF(max), comparisons of these valves with predicted normals for the patient's age, height, etc., and a verbal description of the interpretations of these values. The full report includes a flow volume depiction of the maneuver along with any added comments from the reviewing physician.

The computer analysis proceeds as follows: the central computer receives digitized data representing three flow time curves; each curve is integrated to obtain volumes; each curve is replotted as a flow-volume curve; and the quantities FVC, etc. are calculated. Certain values, as recommended by the published recommendations of the American Thoracic Society are compared to normal values for the patient's identification data according to age, height, and sex; and normals and abnormals are categorized into preliminary disease interpretations according to standard medical diagnostics; and predicted values, and disease categorizations are sent back to the remote unit as soon as they are obtained (0.5-3 minutes). Thoracic Society Standards as used in the present apparatus are set forth in *American Review of Respiratory Disease,* Vol. 119, page 831 (1979).

This analysis is then sent to the editing terminal 154 for physician review and then to the printer plotter 156 for hardcopy print out.

The central computer software processes the flow time data generated by the remote microcomputer to obtain a flow volume curve from the raw data. The flow is sampled at 30 cycles per second to provide a frequency response of at least 15 hertz. It then compares the patient's values with the predicted normal values based on their patient identification data. It also compares values that may have been obtained before medication or intervention was used in the same patient. It provides profiles of longitudinal changes in pulmonary functions, comparing previous tests which have been stored in the computer. It also performs the preliminary interpretations of the values of give a disease catagorization immediately back to the remote unit. It then provides a more extensive interpretation which is printed out for over reading by a chest physician before it is returned with the flow volume curves to the facility using the unit.

The central computer software determines whether curves are adequate or not. It does this by inspecting reproducibility and looking for artifacts at the beginning or at the end of flow volume curves, much as a technician would do. It also looks for reproducibility plus or minus 10% in peak flow and plus or minus 5% in vital capacities with two sequential maneuvers. This indicates good reproducibility and therefore acceptability of curves and any of the instantaneous flows identified at a point or over a portion of expired volume are calculated from the best curve. The best curve is defined as the curve which gives the largest sum of forced vital capacity and FEV1. The acceptability of the curve as mentioned before will be determined by the technician's observation that the subject understood the instructions and performed the test with a smooth continuous exhalation with apparent maximal effort. This is determined by direct observation of the patient and the bar graph for volume. The central computer will detect poor starting maneuvers and also coughing, glotis closure, early termination of expiration, obstruction of the mouth piece during test, unsatisfactory start of recesitation characterized by excessive hesitation, or false start not allowing back extrapolation to time 0, and excessive variability of the three curves. The two best of the three acceptable curves will not vary by more than + or − 10% of the reading, or + or − 100 ml. Predicted values for tests will generally follow regional Thoracic Society standards for vital capacity and FEV 1 and FEF 25 and 75%. The values for instantaneous flow rates on flow volume curves will be taken from Knudsen's study.

Calibration of the remote pulmonary function tester takes place at the central computer site. The central computer asks the operator of the remote unit to perform a calibration routine which involves simply taking a calibrated super syringe at the remote site and attaching it to the sensor and injecting a standard 3.00 liters of air through the sensor at varying rates. The computer then calculates the calibration curve for that remote unit and stores it until calibration is again necessary as determined by combination of length between the last calibration and number of tests since the last calibration stored. This insures that the unit always stays within the specifications for accuracy of flow. Calibration procedures are derived from the American Thoracic Society reccommendations referenced above. Briefly, the vital capacity should be within + or − 3% of the reading or 50 ml, whichever is greater, and the range which the vital capacity at which it can accumulate should be greater than 7 liters. With the present remote unit, the accuracy will be closer to 2% of reading and the vital capacity which it can accumulate is effectively infinite. The flow range is 2 to 14 liters per second and the readings are + or − 5% of reading or 0.1 liters per second whichever is greater for the FEF 25 75% and + or − 5% of reading or 0.2 liters per second of flows at specific volumes on the flow volume curve.

OPERATION

The interconnected solid state devices, as previously described, when programmed according to the attached appendix, provide the following mode of operation:

First, the power is turned on which initiates an automatic reset of all electronics. A question then is shown on display 30 asking for the patient's identification number which is assigned for remote pulmonary function testing purposes, or may be a Blue Cross number, etc. This is entered through the keyboard 28 and the results are continuously shown on the display so that the patient number is displayed after the question asking for patient number entry. Any mistakes are merely typed over using the keyboard in a rotating fashion. Next is a question asking for medications with a medication code or an intervention code used. The next question asked is the patient's age, sex, height in centimeters or inches and body weight in kilograms or pounds. The patient then is instructed on how to perform the maneuver by the display and by the technician or doctor running the test, fitted with nose clips and placed in the sitting position. There is a display signaling the patient to start the maneuver. Then a display showing his total expired lung volume is used to keep the patient blowing at the end of the maneuver. The display provides the technician and the patient with positive feedback for correct maneuver performance. The machine then instructs the operator to get the telephone and put it on the acoustical coupler. This allows the physician or user to utilize existing telephone lines and telephones without any modification and allows pay phones or remote telephones to be used. Alternatively, the data could be stored for one or two maneuvers in the memory and the unit carried to where a telephone is available. Additional remote data storage may be provided with a small digital data recorder. With the data recorder, tests from an entire day could be saved for digital transmission to the central computer in the evening when telephone rates are lower and lines are more available.

When the remote data is to be transmitted, the central computer is contacted by telephone. When an ANSWER carrier is heard the receiver is placed in the acoustic coupler of the modem and the remote unit is signalled by the operator pressing any key on the key pad. The remote unit verifies receipt of the carrier and performs any necessary sign on procedure for the central computer. All of the collected data is transmitted in blocks of ASCII character data with appended error detection information. The blocks contain successively: the remote unit's serial number, all of the collected patient identification information, and the flow rate data. The end of each maneuver is indicated by a special character included on the last block in the maneuver. After the last block in the last maneuver, a special short block consisting only of a "φ" and the associated error detection characters is sent. Each block is acknowledged by an ACK character returned over the line and rejected by a non-acknowledement (NAK) character. The receipt of any other character by the remote unit will cause the remote to break off communication and instruct the operator to place the call again.

The present pulmonary function tester utilizes digital data transmission to lessen telephone time and increase transmission accuracy. Patient identification data is transmitted at 300 baud in about 0.5 sec. Telephone time is further reduced by the prestorage of test maneuvers so that telephone time is only used during actual data transmission. The test data is transmitted typically in about ten seconds, in digital form representing flow rate at 0.03 second intervals. A check sum and the total number of characters sent is transmitted to the central computer so that any digital error caused by noise on the line, etc. is detected.

SOFTWARE APPENDIX

```
\      SYSTEM LEVEL PROGRAM LISTING
\      THIS PROGRAM IS ACTUALLY
\      IMPLEMENTED IN MACHINE LANGUAGE
\      AND REPRESENTED HERE IN A HIGHER
\      LEVEL LANGUAGE ONLY FOR CLARITY

\      SINCE THIS IS BLOCK STRUCTURED CODE START
\      READING AT THE BOTTOM SINCE
\      BASIC PROCEDURES ARE FIRST

\      THE REQUIRED INTRINSICS ARE:
\              GETCH - - GET A CHAR FROM THE KEYS
\              SETIO - - INITIALIZE ALL I/O PORTS
\              SETPOINT - - SET ALL MEMORY REFERENCE
\                  POINTERS TO THE CORRECT INITIAL VALUES
\              TOMODEM - - OUTPUT THE CHAR ARGUMENT TO
\                  THE MODEM
\              TODISP - - OUTPUT THE CHAR ARGUMENT ON THE
\                  DISPLAY
\              WRITELN - - OUTPUT THE STRING ARGUMENT ON
\                  DISPLAY
\              ADDNUM - - ADD A DIGIT TO THE IN MEMORY
\                  DATA ENTRY BUFFER
\              FLOW - - FUNCTION WHICH RETURNS THE CURRENT
\                  FLOW RATE
```

```
const
        RAMEND=(END OF THE AVAILABLE RAM);
        STROM=(START OF THE PROGRAM ROM);
        ENDROM=(END OF THE PROGRAM ROM);
        ENDFILE=(END OF FILE FLAG);
        CR=(CARRIAGE RETURN CHARACTER);
        ACK=(ACKNOWLEDGE CHARACTER);
        NACK=(NON-ACKNOWLEDGE CHARACTER);
        ENTER=(SPECIAL CODE FOR "ENTER" KEY);

var
        DATA,ENTER,TXTPNT : POINTER TO CHAR;
        ERRFLG,FATAL,ENDFLG : BOOLEAN;
        ONCNT,OFFCNT : INTEGERS;

\ TEST RANDOM ACCESS MEMORY
procedure TESTRAM;
var
        RAM : POINTER TO CHAR;

begin
  FATAL:= false ;
  for RAM:=$200,ENDRAM do
    @RAM:=0;
  for RAM:=$200,ENDRAM do
    begin
      if @RAM<>0 then FATAL:= true ;
      @RAM:=$FF;
    end
  for RAM:=$200,ENDRAM do
    if @RAM<>$FF then FATAL:= true ;
end \ TEST READ ONLY MEMORY
procedure TESTROM;
var
        SUM : INTEGER;
        ROM : POINTER TO CHAR;

begin
  for ROM:=STROM,ENDROM do
    SUM:=SUM+@ROM;
  if SUM<>0 then FATAL:= true
  else FATAL:= false ;
end \ DISPLAY THE NEXT QUESTION IN THE LIST
procedure QUESTION;

begin
  repeat
    begin
      TODISP(@TXTPNT);
      TXTPNT:=TXTPNT+1;
    end
  until (@(TXTPNT-1))=CR
end \ MARK THE END OF A MANEUVER
procedure ENDBLOW;

begin
  @DATA:=ENDFILE;
  DATA:=DATA+1;
end
```

```
\ DELETE A MANEUVER
procedure DELETE;

begin
  while @DATA<>ENDFILE do
    DATA:=DATA-1;
end

CHECK FOR START AND STOP OF MANEUVER
boolean function TRIG;

begin
  if FLOW>BASE+0.2 then
    begin
      ONCNT:=ONCNT-1;
      OFFCNT:=16;
    end
  else
    begin
      ONCNT:=16;
      OFFCNT:=OFFCNT-1;
    end ;
end SEND A BLOCK OF DATA
function SEND(POINT);

FOR POINT,TPOINT: POINTER TO CHAR;
    CSUM,NOCHARS: INTEGER;
    REPFLG: BOOLEAN;
begin
  REPFLG:= false ;
  ERRFLG:= false ;
  FATAL = false ;

repeat
    begin
      TOPOINT:=POINT
      CSUM:=0;
      NOCHARS:=0;
      BYTES:=0
      while BYTES<28 do
        begin
          BYTES:=BYTES+1.
          if @TOPOINT<>ENDFILE then
            begin
              TOMODEM(@TOPOINT);
              CSUM:=CSUM+@TOPOINT;
              NOCHARS:=NOCHARS+1,
              TOPOINT:=TOPOINT+1;
            end
          else ;
        end ;
      TOMODEM(NOCHARS);
      TOMODEM(CSUM);
      if @TOPOINT=ENDFILE then
        begin
          CH:=FROMMODEM;
          if CH=ACK then REPFLG:= false
          else if CH=NACK then REPFLG:= true
          else begin
            FATAL:= true ;
            REPFLG:= false ;
          end ;
          if @(TOPOINT+1)=ENDFILE then ENDFLG = true
          else ENDFLG:= false ;
        end ;
```

```
      end
   until REPFLG= false ;
   SEND:=TOPOINT;
end procedure ADDSAMP(VALUE);

begin
   @DATA:=VALUE;
   DATA:=DATA+1;
end

\ MAIN PROGRAM
begin
   \ INITIALIZATION SECTION
   TESTRAM;
   TESTROM;
   SETIO;
   SETPOINT;

\ ACTUAL OPERATION SECTION
   \ ENTER PATIENT ID
   repeat
      begin
         ENDFLG:= false ;
         ENTCNT:=ENTCNT+1;
         @(ENTRY+ENTCNT):=BLANK;
         repeat
            begin
               QUESTION;
               CHAR:=GETCH;
               if CHAR=ENTER then @(ENTRY+ENTCNT):=NUMENT
               else if CHAR=DONE then ENDFLG = true
               else ADDNUM;
            end
         until ENTFLG= true ;
      end
   until ENDFLG= true ;

\ PERFORM PFT
   repeat
      begin
         WRITELN("INHALE THEN BLOW");
         repeat
            begin end
         until TRIG;
         repeat ADDSAMP(FLOW)
         until not TRIG;
         WRITELN("GOOD?");
         if GETCH<>YES then DELETE;
         WRITELN("DONE?");
      end
   until GETCH=YES;

\ TRANSMIT THE DATA
   SIGNON;
   repeat
      SEND(ENTRY)
   until ( not ERRFLG)!FATAL;
   if not FATAL then
      begin
         repeat
            DATA:=SEND(DATA)
         until ENDFLG!FATAL;
      end ;
   GETMES;
end
```

LIST OF INTERPRETATIONS 1. 
2. Restrictive pattern indicated by decreased vital capacity. Measurement of absolute lung volumes and diffusing capacity may confirm restrictive lung disease.

3. Severe obstructive lung disease with air trapping resulting in decreased vital capacity.

4. Moderate obstructive lung disease with air trapping resulting in decreased vital capacity.

5. Mild obstructive lung disease with air trapping resulting in decreased vital capacity.

6. Possible mixed obstructive and restrictive lung disease.

7. Severe obstructive airways disease.

8. Moderate obstructive airways disease.

9. Mild obstructive airways disease.

10. Very mild small airways obstruction which may not be clinically significant.

11. Very mild small airways obstruction which may not be clinically significant.

12. Normal spirometry.

Additional Message:
Suggest bronchodilator therapy and repeat spirometry

What is claimed is:

1. A pulmonary function tester capable of accurately producing, storing, transmitting, receiving and displaying selected information relating to the breathing maneuver of a test subject comprising:
    a remote unit,
    entry means associated with said remote unit for entering test subject data;
    means communicating with said remote unit for accepting the breathing maneuver of a test subject,
    means communicating with said accepting means for producing electrical signals proportional to the flow rates of the breathing maneuver of the test subject;
    digitizing means communicating with said signal production means for converting the signals produced by the flow rates from the breathing maneuver into digital form representative of expiration flow rate and expiration time;
    read/write memory means communicating with said entry means and said digitizing means for retrievably storing the test subject data entered through said entry means, and digitized test subject data from said digitizing means,
    communication interface means communicating with said digitizing means and said read/write memory means for communication of signals including digitized test subject data, to and from at least one locus external to said remote unit,
    display means communicating with said digitizing means, said rear/write memory means, said entry means and said communication interface means, for the display of test subject data, entry data and communications fed back to said communication interface means; and
    computer processing means for controlling the functioning of said remote unit including the representations displayed by said display means and responsive to preselected criteria obtained from said read/write memory, means said communication interface means and input from said entry means, and the sequence of function and manner of function of said communication interface means and said read/write memory means, so as to provide data on a test subject breathing maneuver which compares test subject flow rates with total expired volume for the subsequent diagnostic interpretation of pulmonary function.

2. The pulmonary function tester of claim 1 wherein said accepting means includes pressure transducing means capable of converting changes in pressure during the breathing maneuver of a test subject into electrical signals proportional to flow rates.

3. The pulmonary function tester of claim 1 wherein said display means includes a plasma display.

4. The pulmonary function tester of claim 1 wherein said communication interface means includes means for simultaneously transmitting and receiving a serial stream of signals to and from at least one locus remote from said remote unit and means for converting said serial stream of signals into a form suitable for use by said display means.

5. The pulmonary function tester of claim 4 wherein the serial stream of signals includes signals representative of calculated volume and comparisons the predicted normal values and acceptance criteria for breathing manuevers suitable for pulmonary function diagnosis that enables acceptable test subject flow rate and total expired volume to be displayed for subsequent medical interpretation.

6. A method of measuring pulmonary function comprising:
- sensing pressure generated by test subject expiration into a remote unit;
- converting the pressure sensed to an electrical signal proportional to the flow rates of test subject expirations, digitizing said electrical signal to produce a digitized signal;
- storing the digitized signal in a read/write memory in the remote unit;
- transmitting said digitized signal in a serial data stream to a central computer;
- converting said serial data stream into a form suitable for subsequent computation use at the central computer;
- computing pulmonary function values at the central computer that are indicative of flow rates and volume from the converted serialized data stream;
- transmitting said pulmonary function values in a serial data stream to the remote unit and displaying the pulmonary function values in a manner suitable for diagnostic interpretation.

7. The method of claim 6 further comprising the step of entering and storing test subject data into said read/write memory prior to transmitting data to a central computer.

8. The method of claim 7 further comprising the step of comparing the computed pulmonary function values from only successful test subject maneuvers with predicted pulmonary function values derived from the test subject data and predetermined and preselected norms to produce further values indicative of test subject pulmonary function.

* * * * *